US012714415B2

(12) United States Patent
Clement et al.

(10) Patent No.: US 12,714,415 B2
(45) Date of Patent: Aug. 25, 2026

(54) ANCHOR HOLDER, KIT FOR ATTACHING AT LEAST ONE SUTURE THREAD AND ASSEMBLY METHOD

(71) Applicant: S.B.M., Lourdes (FR)

(72) Inventors: Denis Clement, Omex (FR); Matthieu Souque, Tarbes (FR); Celine Magnus Courtade-Jouanicq, Barzun (FR); Matthieu Viveau, Tarbes (FR)

(73) Assignee: S.B.M., Lourdes (FR)

( * ) Notice: Subject to any disclaimer, the term of this patent is extended or adjusted under 35 U.S.C. 154(b) by 223 days.

(21) Appl. No.: 18/378,824

(22) Filed: Oct. 11, 2023

(65) Prior Publication Data

US 2024/0173025 A1 May 30, 2024

(30) Foreign Application Priority Data

Nov. 28, 2022 (FR) ..................................... 22 12421

(51) Int. Cl.
*A61B 17/04* (2006.01)

(52) U.S. Cl.
CPC .. *A61B 17/0401* (2013.01); *A61B 2017/0409* (2013.01); *A61B 2017/044* (2013.01)

(58) Field of Classification Search
CPC .... A61B 2017/0416; A61B 2017/0053; A61B 2017/0409; A61B 2017/0414; A61B 2017/044
See application file for complete search history.

(56) References Cited

U.S. PATENT DOCUMENTS 5,478,345 A * 12/1995 Stone ................. A61B 17/0469 221/113
5,755,729 A * 5/1998 de la Torre ........ A61B 17/0469 606/139
5,894,921 A * 4/1999 Le ...................... A61B 17/0401 206/63.3
5,944,739 A * 8/1999 Zlock ..................... A61B 17/17 606/232
11,375,992 B1 * 7/2022 Zenz-Olson .......... A61F 2/0811
2007/0162052 A1 * 7/2007 Hashimoto ........ A61B 17/0469 606/139
2008/0275474 A1 11/2008 Martin
2011/0202074 A1 * 8/2011 Talmo ................ A61B 17/0401 606/228

(Continued)

OTHER PUBLICATIONS

French Search Report dated Jun. 11, 2023.
French Opinion on Patentability Nov. 28, 2022.

*Primary Examiner* — Alexander J Orkin
(74) *Attorney, Agent, or Firm* — IPSILON USA, LLP

(57) ABSTRACT

An anchor holder (10) for at least one suture thread (12) in a biological tissue has an anchor (11) connected to at least one suture thread (12). A casing (13) includes a housing (14) in which the anchor (11) is stowed, the head of the anchor (11) being positioned coaxial with the first opening (140) of the housing (14) with a view to assembly with an assembly end of an attachment guide. A reel (15) if provided for stowing the suture thread (12) and being in communication with the housing (14) so as to allow the passage of the suture thread (12). At least one locking member is provided, (16) which in an activated state, prevents the anchor (11) from coming out of the casing (13) and the suture thread (12) from being released.

16 Claims, 9 Drawing Sheets

(56) References Cited

U.S. PATENT DOCUMENTS

| | | | | |
|---|---|---|---|---|
| 2012/0109155 | A1 | 5/2012 | Robinson | |
| 2013/0023919 | A1* | 1/2013 | Olivera | A61F 2/9525 53/235 |
| 2013/0325063 | A1* | 12/2013 | Norton | A61B 17/0401 606/232 |
| 2016/0000422 | A1* | 1/2016 | Harrison | A61B 17/0491 606/144 |

* cited by examiner

[Fig. 1]
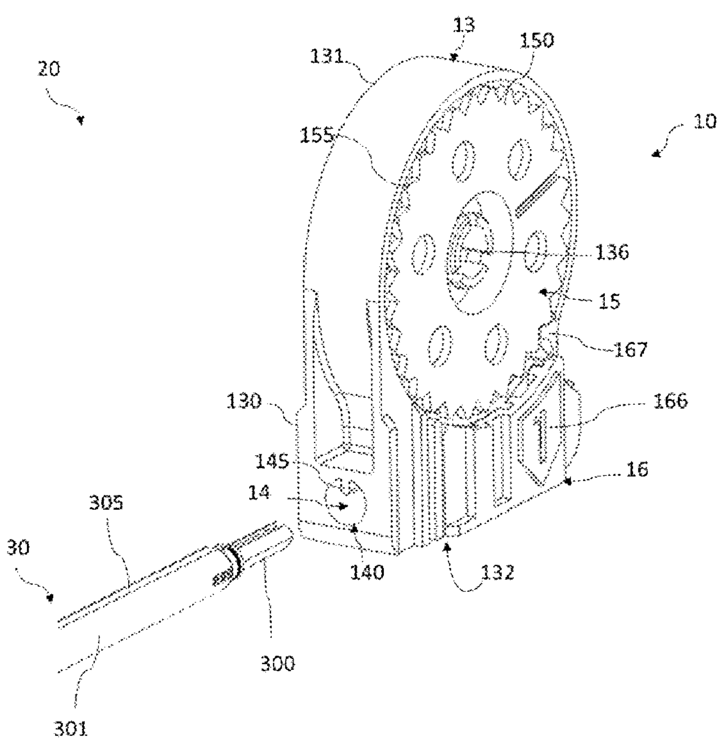
[Fig. 2]
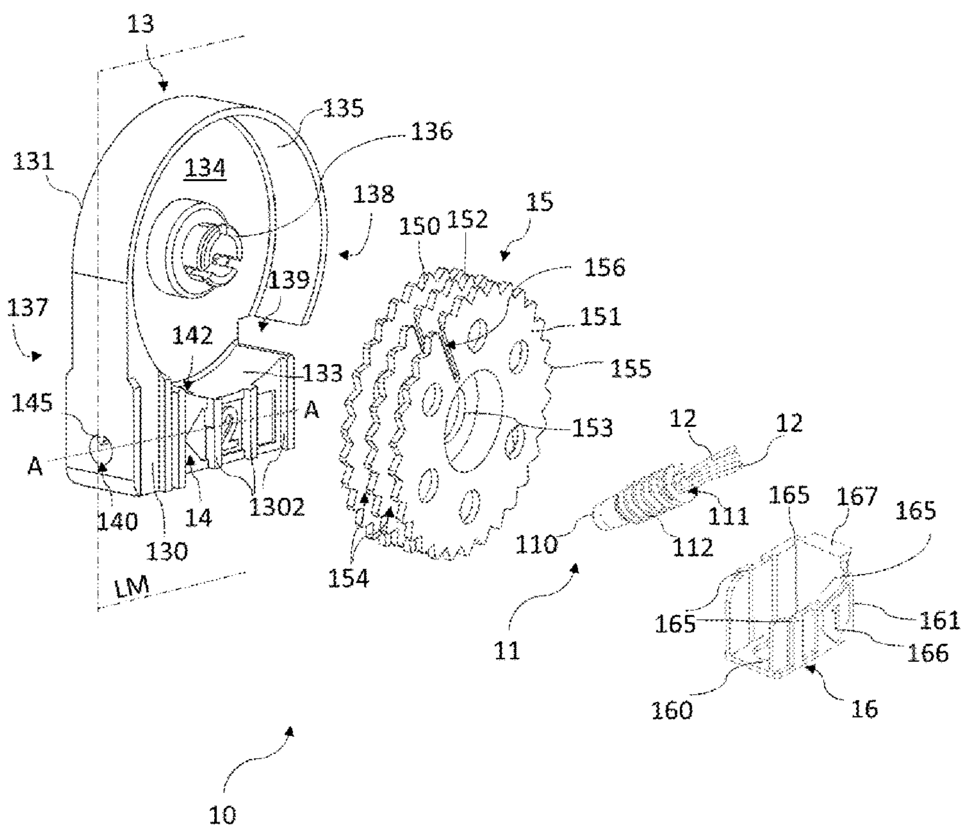

[Fig. 3]
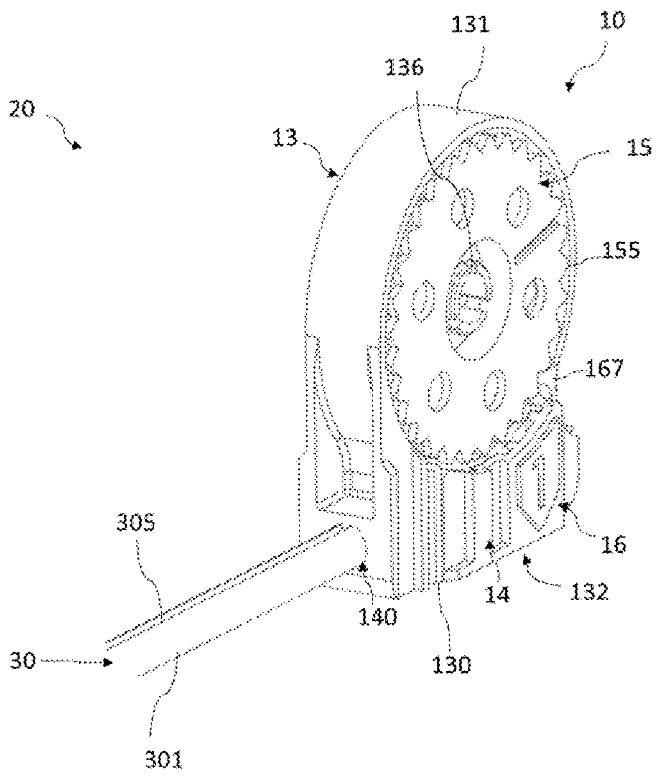
[Fig. 4]
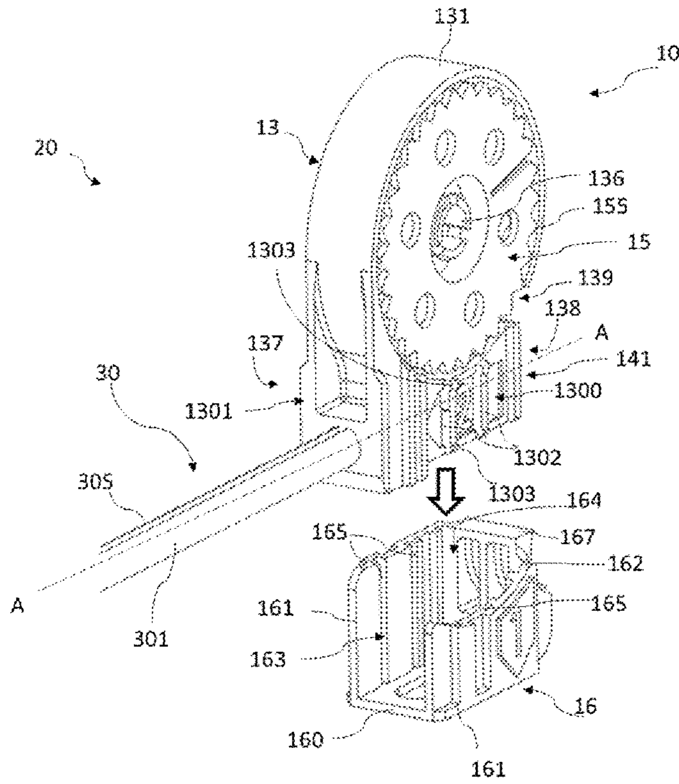

[Fig. 5]
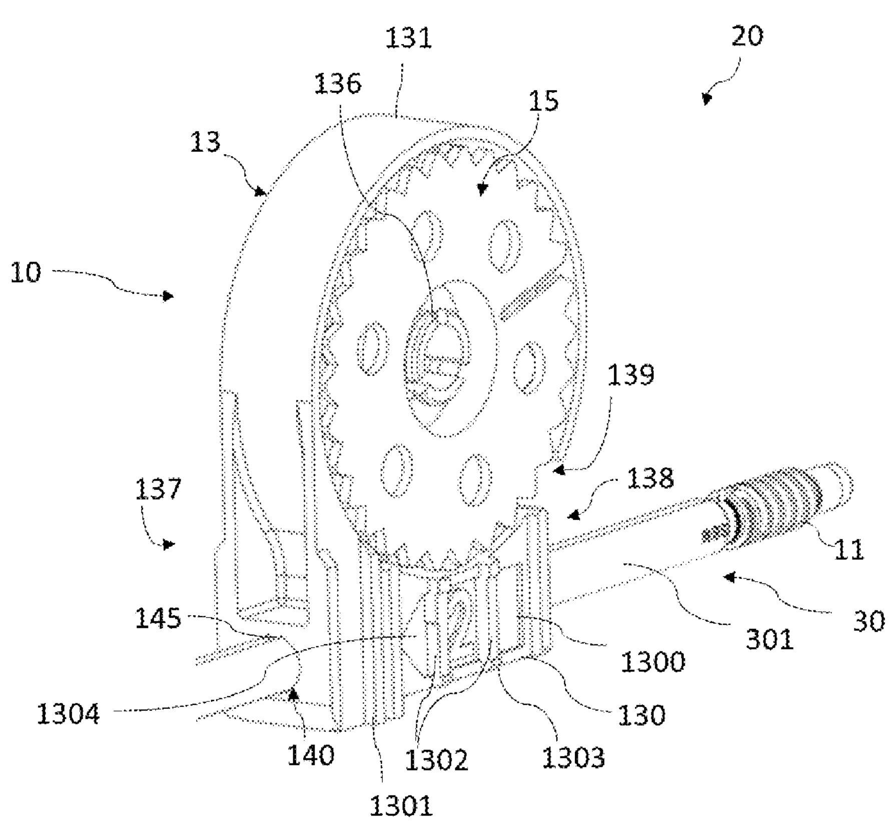
[Fig. 6]
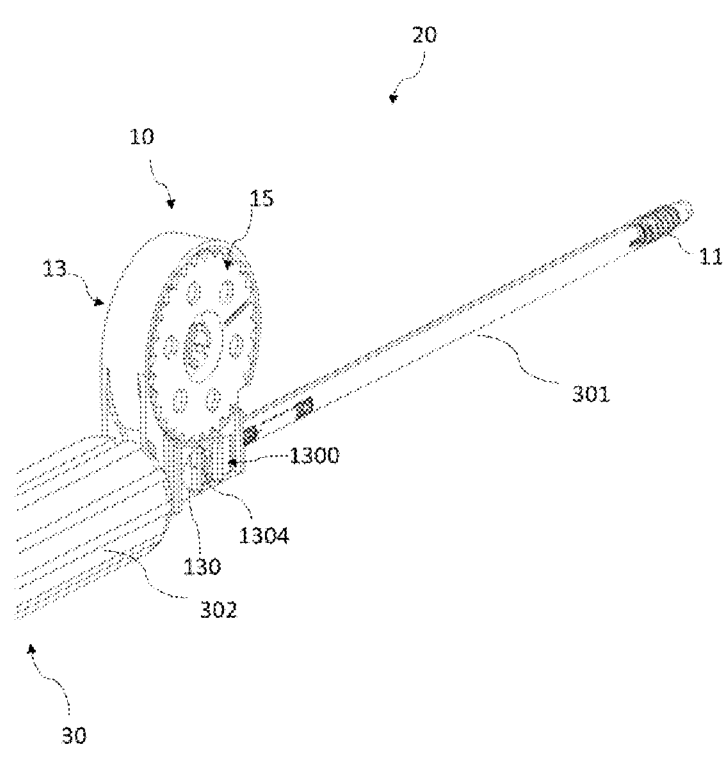

[Fig. 7]
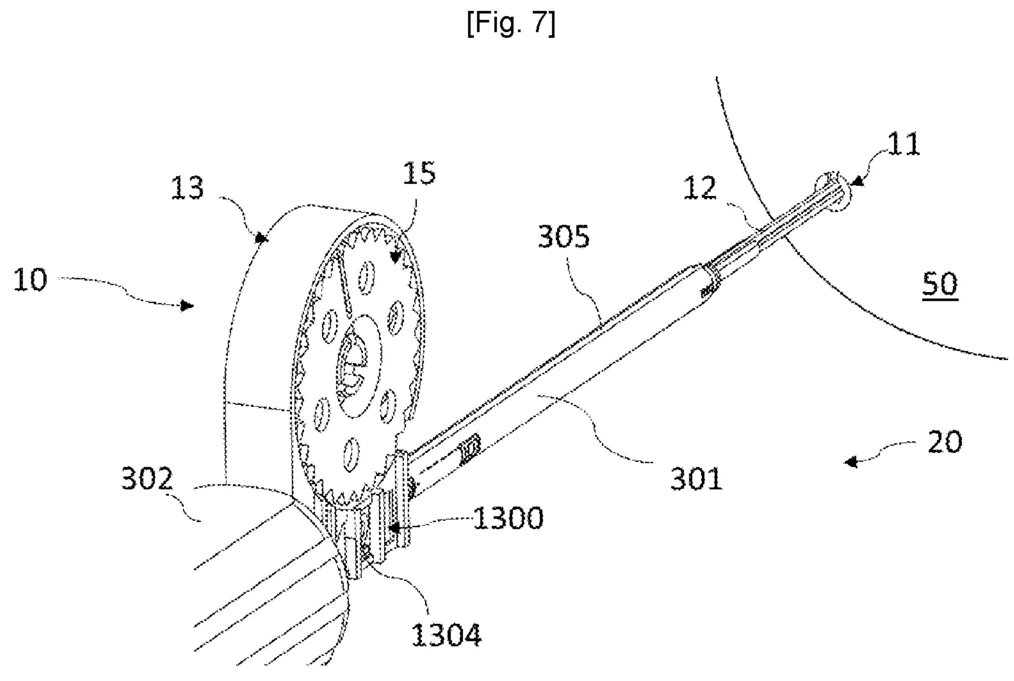
[Fig. 8]
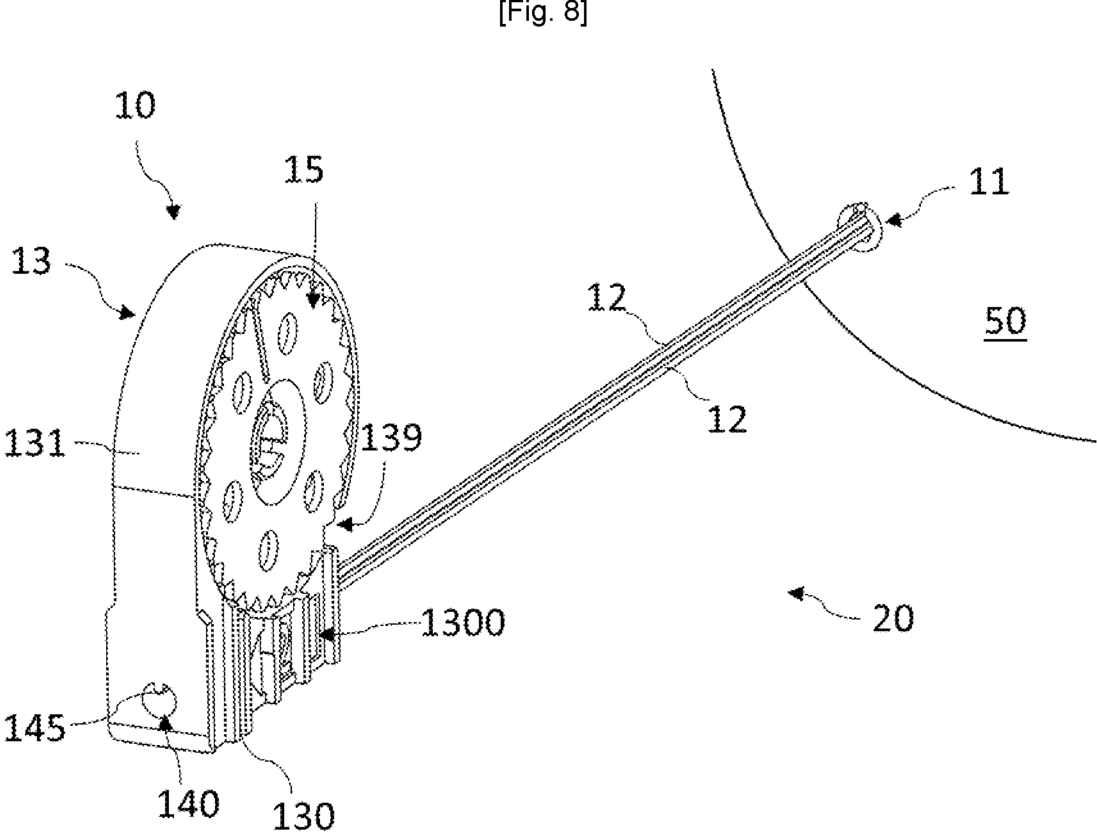

[Fig. 9]
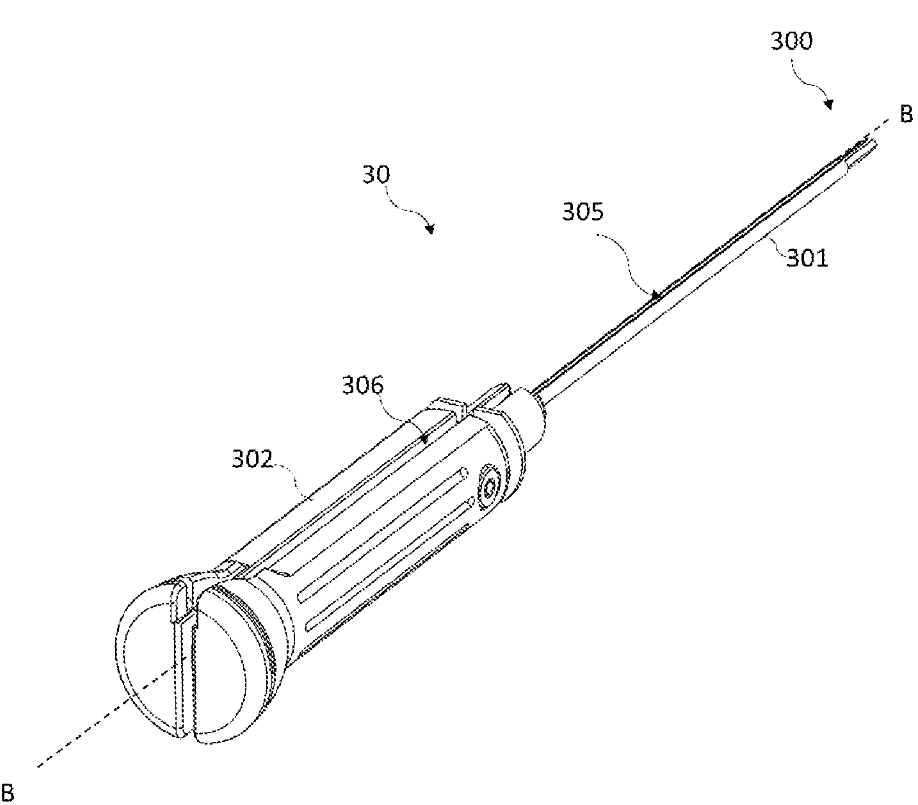
[Fig. 10]
15
131
10
136
137
145
C
C
140
130
132

[Fig. 11]
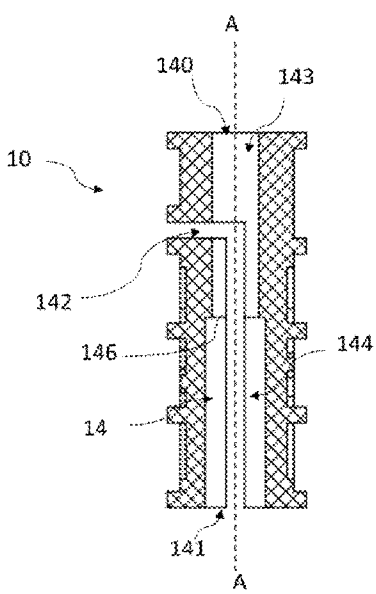
[Fig. 12]
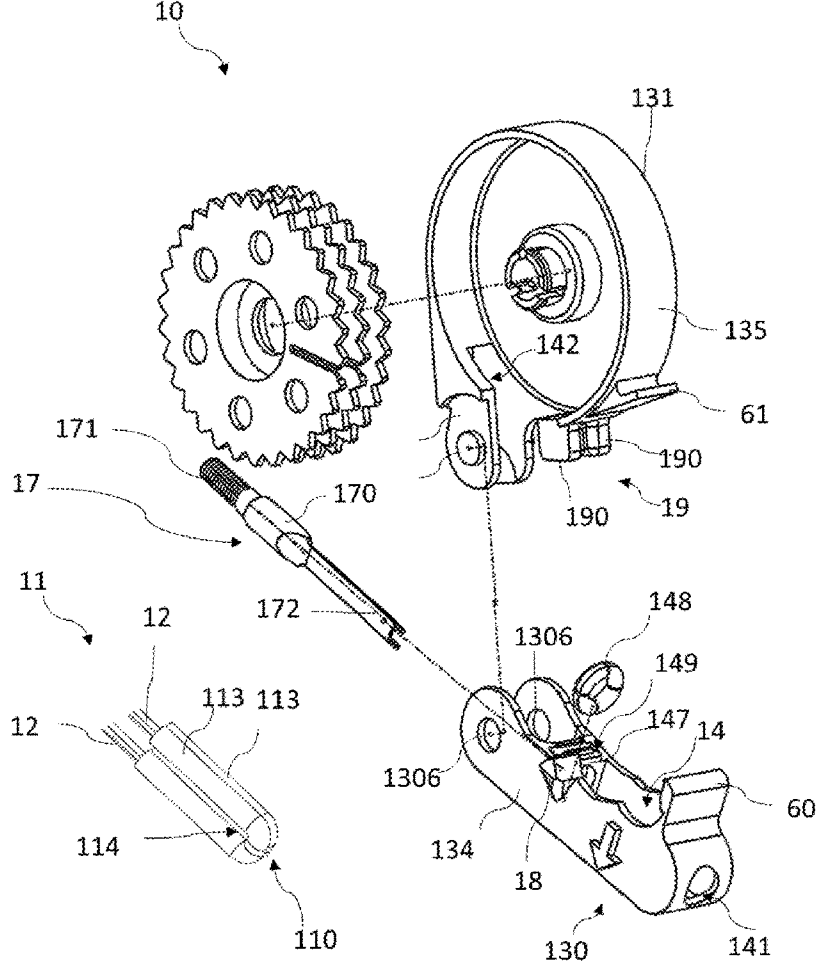

ANCHOR HOLDER, KIT FOR ATTACHING AT LEAST ONE SUTURE THREAD AND ASSEMBLY METHOD

RELATED APPLICATION

This application claims the benefit of priority from French Patent Application No. 22 12421, filed on Nov. 28, 2022, the entirety of which is incorporated by reference

TECHNICAL FIELD

The invention relates to an anchor holder for at least one suture thread in at least one biological tissue of a human or animal body. The biological tissue may be a bone tissue or a soft tissue such as a tendon or a ligament. More generally, the present invention relates to the field of surgery, especially orthopedic surgery. In particular, the device according to the invention makes it possible to bring together and attach at least two tissues that are distinct from one another, alternatively it is also possible to bring together and attach at least two parts of the same soft tissue, for example two parts of a meniscus.

More particularly, the anchor which is stowed in the anchor holder makes it possible to attach ligaments or tendons to a bone via a surgical operation on the shoulder, the knee, the hip, the hand, the foot, the elbow, the ankle or the spine. In this type of surgery, it is sought to ensure in particular the reliability of attachment of the sutures, a reduction in the operating time, as well as a reduction in the invasiveness of the operation. Behind these aspects, the main aim is to reduce the length of time taken for postoperative convalescence and lower the risk of complications linked to the use of an anchor to treat patients. To these ends, practitioners currently favor arthroscopy techniques, with which the invention is compatible.

PRIOR ART

Quite a few attachment kits for suture thread address these issues of reliability, reduction in operating time, and reduction in the invasiveness of the operation.

In general, such an attachment kit comprises an anchor, also referred to as an implant, to which one or more suture threads may be connected. For example, an anchor may be equipped with two or three suture threads which are each rigidly secured to the anchor. The anchor may also carry a suture strip. Thus, in the rest of this document, the term "suture thread" designates either a suture strip or a suture thread.

Moreover, an attachment kit for suture thread also includes a guide called a "driver" in the jargon of those skilled in the art. This guide usually has a sleeve which is extended by a rod to the end of which the anchor is fastened, removably. To prevent the suture threads from getting caught in the patient's soft tissue as the anchor is screwed in during an arthroscopy, the attachment guide may have a splined passage or a lateral groove so as to hold the suture threads against or in the attachment guide. Document EP 2 779 913 illustrates an example of this type of attachment kit comprising a splined guide.

To optimize surgical operating times, surgeons want to limit the time it takes to mount the anchor on the attachment guide. To this end, an attachment kit is currently industrially produced in which each anchor is premounted on an attachment guide.

In practice, the suture threads are assembled to the anchor then the anchor is mounted on the attachment guide and the suture threads may be wound on the sleeve of the attachment guide thus constituting the attachment kit. Assembly of the attachment kit is carried out in a white room, and once assembled the kit is packaged, and the attachment kit and its packaging are then sterilized.

Thus, during a surgical operation, the practitioners open the packaging at the last minute during the operation to preserve the sterility of the attachment kit. The fact that the anchor is supplied premounted on the attachment guide makes it possible to save time during the operation, but after the insertion of the anchor in the bone tissue of the patient, the guide is systematically disposed of and treated as medical waste. By way of example, an operation to repair the rotator cuff of the shoulder, the aim of which is to repair tendons that have become detached from the shoulder, on average requires the use of four to six anchors and thus the same number of guides are thrown away. Given that a surgeon may operate on between fifteen and twenty patients per week, this generates a considerable amount of waste.

The invention aims to overcome all of these drawbacks.

SUMMARY OF THE INVENTION

The invention aims to provide a technical solution to repair ligaments or tendons efficiently while reducing the amount of medical waste associated with this type of operation.

To this end the present invention relates to an anchor holder for at least one suture thread in a biological tissue, the anchor holder comprising:

- an anchor equipped with an assembly head, the anchor being connected to the suture thread,
- a casing including a housing in which the anchor is stowed in a predetermined position, the housing comprising a first opening, the assembly head of the anchor being positioned coaxial with the first opening with a view to inserting in the housing an assembly end of an attachment guide, the assembly end of the guide being complementary to the assembly head of the anchor,
- a reel which is configured to stow and release the suture thread, the reel being in communication with the housing so as to allow the passage of the suture thread, and
- at least one locking member which has, on the one hand, an activated state preventing the anchor from coming out of the casing and the suture thread from being released, and on the other hand, a deactivated state allowing the anchor to come out of the casing and the release of the suture thread.

The anchor holder according to the invention makes it possible to provide practitioners with an anchor connected to suture thread and stowed in a casing, advantageously, the anchor is ready to be assembled quickly with an attachment guide. To be specific, the first opening of the housing allows a suitable attachment guide to fit on the head of the anchor. The anchor holder according to the invention thus provides a solution for simple and quick mounting of the anchor on the attachment guide while also offering a solution for easily controlling the release of the suture thread. It is thus possible to supply an anchor premounted in the anchor holder of the invention and to use a reusable and sterilizable attachment guide. In this regard, the present invention helps reduce the amount of medical waste produced during orthopedic surgery, while still allowing the surgical operation to be performed quickly.

In some embodiments, the reel may be mounted rotatably about an axis and include at least one toothed wheel. This makes it possible to stow the suture thread and to release same easily during the operation.

In some embodiments, the locking member may include a stop which interacts with the toothed wheel so as to block the rotation of the reel.

In some embodiments, the reel may comprise at least one circular groove around which the suture thread is wound.

In some embodiments, the housing may pass right through the casing between the first opening and a second opening opposite and coaxial with the first opening, the anchor being positioned close to the second opening. It is thus possible to slide the rod of the attachment guide in the housing and thereby unwind the thread parallel to the rod of the attachment guide.

In some embodiments, the locking member obstructs the second opening. This makes it possible to limit the risk of the anchor coming out of the housing accidentally.

In some embodiments, the locking member may be detachable from the casing, and in this configuration, the locking member goes into its deactivated state when it is detached from the casing. The detachable nature of the locking member makes it possible to easily release the anchor and the suture thread.

In some embodiments the anchor holder may include a poka-yoke arranged in the housing at least in the first opening so as to insert the assembly end of the attachment guide with a predetermined orientation to allow assembly with the head of the anchor. The poka-yoke improves the precision of assembly of the attachment guide and of the anchor through the housing. The poka-yoke also ensures the translational movement of the anchor holder on the rod of the attachment guide when the locking member is in the deactivated state. In particular, according to one embodiment, the rod of the attachment guide may include a longitudinal slot, the poka-yoke then acting as a slider for guiding the movement of the casing by sliding in the slot.

In some embodiments, the poka-yoke is formed of a ridge which extends longitudinally along the axis of the housing.

In some embodiments, the housing is mounted rotatably relative to the casing, the housing is movable, on the one hand, between an open position in which the housing is radially at a distance from the reel, and on the other hand, a closed position in which the housing is connected to the reel, and when the housing is in the closed position, the locking members are in their activated state and when the housing is in the open position, the locking members are in their deactivated state. This embodiment makes it possible to take on an anchor in tissue mounted on an interface with a view to attaching the suture threads with the aid of an impactor.

The present invention also relates to an attachment kit for attaching at least one suture thread to a biological tissue, the attachment kit comprising an anchor holder according to the invention and a sterilizable and reusable attachment guide which includes a sleeve extended by a rod ending in an assembly end configured to be assembled with the assembly head of the anchor which is stowed in the housing of the anchor holder. The attachment kit provides a technical solution allowing simple and quick assembly of the anchor on the attachment guide. In this regard, the attachment kit also addresses the technical problem by reducing waste through the use of a reusable attachment guide.

In some embodiments, the anchor holder may be movable in translation on the rod of the attachment guide when the housing slides on the rod. This makes it possible to mount the anchor on the attachment guide with precision and to place the suture thread under tension.

In some embodiments, the attachment kit comprises holding means which are configured to hold the suture thread close to the rod or against the rod.

In some embodiments, the holding means include a slot which extends longitudinally
on the attachment guide, the slot being configured to receive the suture thread when the anchor holder is moved toward the sleeve on the rod of the attachment guide.

The present invention uses a sterilizable and reusable attachment guide adapted to be used with an anchor holder defined according to the present invention. To this end, the attachment guide is characterized in that it includes a sleeve and a rod which extends longitudinally from the sleeve toward an assembly end, the assembly end being configured to be assembled to the assembly head of the anchor. The attachment guide may include holding means which are configured to hold the suture thread close to the rod or against the rod. For example, the holding means may be formed by a slot which extends longitudinally at least between the assembly end of the rod and the sleeve.

The attachment guide is adapted to interact with the casing of the anchor holder insofar as the attachment guide is configured to receive the housing sliding on the rod from the assembly end toward the sleeve. In parallel, the holding means make it possible to hold the suture thread close to the rod or against the latter. This makes it possible to prevent the threads from coming into contact with soft tissue when the surgeon inserts the anchor in the bone tissue under arthroscopy. For example, the holding means may comprise a slot made in the attachment guide which is configured to receive the suture thread which is released by the reel when the casing moves on the rod.

The attachment guide is moreover configured to interact with the anchor holder of the invention so as to mount, precisely, simply and quickly, the anchor on its assembly end.

The invention further relates to an assembly method for assembly of an attachment guide and of an anchor equipped with at least one suture thread and configured to be inserted in a biological tissue, the anchor and the suture thread being stowed in an anchor holder which includes:

- a housing receiving the anchor in a predetermined position,
- a reel which stows the suture thread and is in communication with the housing so as to allow the passage of the suture thread from the reel to the housing, and
- at least one locking member which prevents release of the anchor and of the suture thread in an activated state.

The attachment guide used in the assembly method is sterilizable and reusable, and in particular, the attachment guide includes a sleeve, a rod which extends longitudinally from the sleeve to an assembly end.

The assembly method according to the invention comprises the following steps:

- assembling the assembly end of the rod with the anchor, the assembly end of the rod of the sterilized attachment guide being inserted in the housing of the anchor holder,
- deactivating the locking member in order to release the anchor and the suture thread, and
- moving the anchor holder on the rod in the direction of the sleeve, the anchor holder sliding via the housing on the rod, in such a way as to place the suture thread under tension between the assembly end of the attachment guide and the anchor holder sliding on the rod.

The assembly method also makes it possible to address the technical problem in particular using a sterilizable attachment guide and an anchor holder which makes it possible to mount the anchor on the attachment guide while controlling the tensioning of the suture thread, simply and quickly.

BRIEF DESCRIPTION OF THE DRAWINGS

Further features and advantages of the invention will emerge from reading the description below. This description is purely illustrative and should be interpreted in light of the attached drawings, in which:

FIG. 1 is a perspective view of an attachment kit for attaching at least one suture thread to soft tissue, in accordance with the invention, the attachment kit comprising an anchor holder and an attachment guide.

FIG. 2 is an exploded view of the anchor holder for at least one suture thread which is visible in FIG. 1.

FIG. 3 depicts a step of an assembly method according to the invention and which uses the attachment kit of FIG. 1, the attachment guide being inserted in a housing of the anchor holder so as to come into contact with the anchor stowed in the anchor holder.

FIG. 4 depicts another step of the assembly method, in which the locking member is in a deactivated state in which the anchor and the suture thread may be released.

FIG. 5 depicts a step of the assembly method, in which the anchor is positioned at the assembly end of the rod of the attachment guide while the anchor holder is moved in the direction of the sleeve of the attachment guide.

FIG. 6 depicts a step of the assembly method, in which the anchor is positioned at the assembly end of the rod of the attachment guide while the anchor holder is moved in the direction of the sleeve of the attachment guide.

FIG. 7 is a perspective view of the attachment kit, the anchor of the kit is inserted in bone tissue, the anchor holder being positioned on the attachment guide while some of the suture thread is still stowed on the reel of the anchor holder.

FIG. 8 is a perspective view of the anchor holder which still stows some of the suture thread on the reel while the anchor is inserted in bone tissue, the attachment guide being separated from the housing of the anchor holder.

FIG. 9 is a perspective view of the attachment guide according to the invention.

FIG. 10 schematically depicts the front face of the anchor holder of FIG. 1.

FIG. 11 schematically depicts a cross section C-C through the anchor holder of FIG. 10, the cross section C-C extending more specifically through the housing of the anchor holder.

FIG. 12 is an exploded view of another embodiment of the anchor holder, in which the anchor is a soft anchor.

Figures 13, 14:
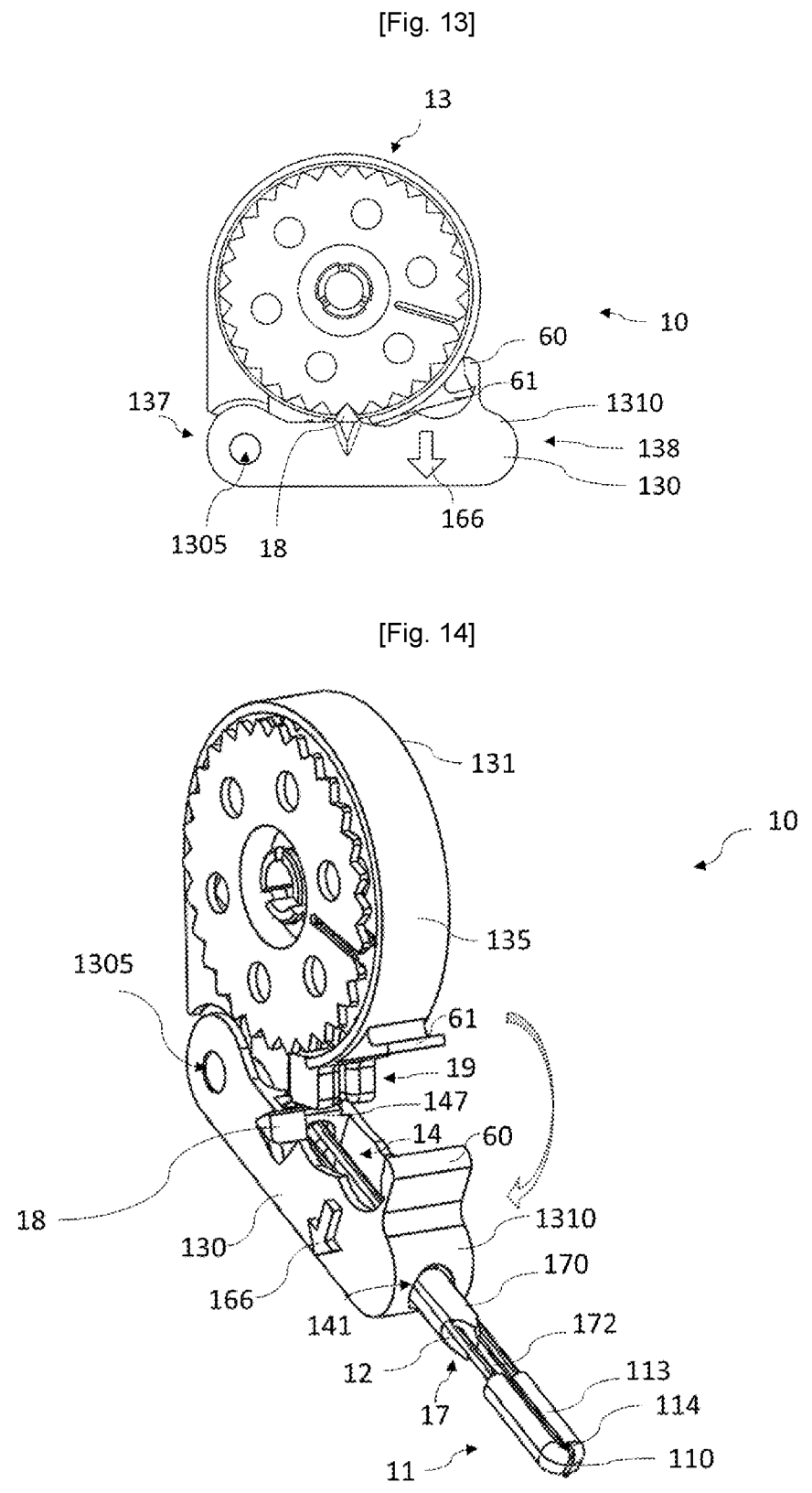

FIG. 13 is a side view of the anchor holder of FIG. 12, in which the locking member is in its activated state.

FIG. 14 is a side view of the anchor holder of FIG. 12, in which the locking member is in its deactivated state, the anchor is released and emerges from the housing 14 with a view to its insertion in bone tissue.

FIG. 15 depicts in perspective a lateral view of the anchor holder of FIG. 12 in which the base is not shown so as to depict the way in which interface supporting the anchor in tissue is held in place.

FIG. 16 is a side view of the anchor holder of FIG. 12, in which the locking member is in its deactivated state.

FIG. 17 schematically depicts a flow chart illustrating a method for assembling an anchor on an attachment guide according to the invention.

DETAILED DESCRIPTION OF THE EMBODIMENTS

With reference to FIGS. 1 to 8 and 10 to 16, the invention relates to an anchor holder 10 for anchoring at least one suture thread 12 in biological tissue. The anchor holder 10 is used in particular for the repair of soft tissue such as ligaments and tendons. It makes it possible to reinforce or attach the insertions of this soft tissue in the bone tissue 50 of a patient.

According to one embodiment of the invention and as shown in FIGS. 1 and 3 to 9, the anchor holder 10 forms part of an attachment kit 20 which also includes an attachment guide 30 which also forms part of the invention.

In this regard, the anchor holder 10 comprises an anchor 11 which is connected to at least one suture thread 12. According to one embodiment, the anchor 11 may be alternatively connected to a suture strip, one suture thread, two suture threads or indeed three suture threads. According to one embodiment, the suture thread 12 may include needles with a view to ligating the soft tissue. In practice, the surgeon chooses to use one or other of these anchors 11 depending on the operation to be performed. In the example of FIGS. 2, 7 and 8, the anchor 11 is connected to two suture threads 12 which are linked to the anchor 11 and extend out and back again. This is why four filaments can be seen in these figures, corresponding in reality to two suture threads 12.

As can be seen more clearly in FIG. 2, the anchor 11 comprises a distal end 110 which is configured to be inserted to the bottom of a pre-bore drilled in the bone tissue. To this end, the distal end 110 is extended by a cylindrical portion. Furthermore, the anchor 11 comprises a proximal end 111 which corresponds to the assembly head of the anchor 11. The proximal end 111 is referred to as "proximal" since it allows interaction with the attachment guide 30. The proximal end 111 of the anchor 11 includes a blind hole inside which are the attachment means for the suture thread 12. The attachment means may for example consist of an eyelet arranged in the blind hole of the anchor 11.

Moreover, the blind hole has an opening having a cross section of predetermined shape for example, as shown in FIG. 2 said cross section is hexagonal. However, the cross section may have a different geometric shape, for example polygonal, such as a triangle, rectangle, trapezium, pentagon, and the like. Note that the cross section of the opening of the blind hole may be different from the cross section of the cavity of the hole. To sum up, it can be said that the assembly head of the anchor 11 has a predetermined shape. As can be seen in FIGS. 2, 5 and 6, the proximal end 111 is extended by a threaded portion 112. The threaded portion 112 makes it possible, first of all, to screw the anchor 11 into the bone tissue 50 with the aid of the attachment guide 30, and secondly, to retain the anchor 11 in the bone tissue 50.

The anchor holder 10 further includes a casing 13 which is configured to stow the anchor 11 and the suture thread 12. The anchor holder 10 may also be considered to be an implant holder, in which case the anchor 11 corresponds to the implant.

In the example shown in FIGS. 1 to 8, the casing 13 has two parts, a base 130 which includes a housing 14 for the anchor 11 and a receptacle 131 which supports a reel 15. In this instance, the receptacle 131 is cylindrical and lies above the base 130 which is positioned in the lower part of the casing 13. Thus, the base 130 includes a lower face 132 which delimits the casing 13 at the bottom, and an upper face 133 which forms a junction with the receptacle 131 (see FIG. 2). The upper face 133 is convex relative to the lower face 132. The base 130 extends in a longitudinal direction along a longitudinal axis A-A.

As shown in FIG. 2, the receptacle 131 extends radially around an axis which is perpendicular to the longitudinal axis A-A. In this example, the receptacle 131 comprises a lateral wall 134 and a peripheral wall 135. The lateral wall 134 extends radially around the axis of the receptacle 131 and defines the end wall of the latter which is configured to receive the reel 15. The peripheral wall 135 extends from the peripheral rim of the lateral wall 134 so as to define a cylinder about the axis of the receptacle 131. In the lower part of the receptacle 131, the peripheral wall 135 coincides with the upper face 133 of the base 130. Lastly, the width of the peripheral wall 135 defines the depth of the receptacle for the reel 15. Moreover, so as to receive the reel 15, the receptacle 131 comprises reception means 136. In this instance, the reception means 136 extend along the axis of the receptacle 131. In the embodiment shown in FIGS. 1 to 8, the reception means 136 consist of a rotation shaft. However, the reception means 136 may take another form and be arranged differently within the receptacle 131.

In the example of FIGS. 1 to 8, the receptacle for the reel 15 is thus open on a face opposite the lateral wall 134 which constitutes the end wall of the receptacle 131. Nevertheless, as an alternative, the receptacle 131 may also comprise an openable lid for closing off the receptacle for the reel 15.

According to one embodiment, the housing 14 makes it possible to stow the anchor 11 in a predetermined position. As shown in FIGS. 2 and 11, the housing 14 extends longitudinally along the longitudinal axis A-A. For example, the housing 14 may be of cylindrical shape. In particular, the housing 14 may pass right through the casing 13 between a first opening 140 and a second opening 141 (see FIG. 11). In this instance, the second opening 141 is opposite and coaxial with the first opening 140, the anchor 11 being positioned close to the second opening 141. The first opening 140 is positioned on a front face 137 of the casing 13 while the second opening 141 is positioned on a rear face 138 of the casing 13 (see in particular FIGS. 2, 4, 10 and 11). Thus, the housing 14 may be cylindrical and have a longitudinal cavity 143 which extends right through the casing 13 along a longitudinal axis A-A from the front face 137 to the rear face 138 of the casing 13.

The casing 13 further comprises two flanks, on the one hand, a closed flank corresponding to the lateral wall 134 of the receptacle 131 extended by the base 130, and on the other hand, an open flank which is defined by the opening of the receptacle 131 and the base 130 which extends same. The open flank makes it possible to remove the reel 15 from the receptacle 131 easily. Alternatively, as stated above, the open flank may include an openable lid.

In this example, the head of the anchor 11 is positioned coaxial with the first opening 140. This makes it possible to use the first opening 140 to insert in the housing 14 an assembly end 300 of the attachment guide 30. Note that the assembly end 300 of the attachment guide 30 is configured to be assembled to the head of the anchor 11. In the example shown in FIG. 11, the housing 14 includes an accommodating portion 144 which is proximal to the second opening 141. The accommodating portion 144 has dimensions greater than the rest of the cavity 143 so as to accommodate the anchor 11. A flange 146 defines the demarcation between the accommodating portion 144 and the rest of the cavity 143 which opens out at the first opening 140. The assembly head of the anchor 11 is positioned in abutment with the flange 146 so as to be positioned to receive the assembly end 300 of the attachment guide 30.

As shown in FIGS. 1, 2, 6, 8 and 10, the anchor holder 10 comprises a poka-yoke 145. The poka-yoke 145 is arranged in the housing 14 at the first opening 140. The poka-yoke 145 may also extend longitudinally right through the casing 13. As can be seen in FIG. 2, the poka-yoke 145 extends parallel to the longitudinal axis A-A in a median longitudinal plane LM of the casing 13. The poka-yoke 145 makes it possible to insert the assembly end 300 of the attachment guide 30 with a predetermined orientation to allow assembly with the head of the anchor 11.

According to one embodiment, the poka-yoke 145 consists of a ridge which extends longitudinally and parallel to the axis A-A of the housing 14. The ridge protrudes inside the cavity of the housing 14.

As shown in FIGS. 1 to 4, the anchor holder 10 comprises at least one locking member 16 which makes it possible to retain the anchor 11 in the housing as well as to prevent release of the suture thread 12 which is stowed on the reel 15. To this end, the locking member 16 has an activated state and a deactivated state.

FIGS. 1 and 3 show an anchor holder 10 in which the locking member 16 is in its activated state. This state prevents the anchor 11 from coming out of the casing 13 and the suture thread 12 from being released. In practice, in its activated state the locking member 16 obstructs the second opening 141 of the housing 14.

Conversely, FIG. 4 shows an anchor holder 10 in which the locking member 16 is in a deactivated state. This state allows the anchor 11 to come out of the casing 13 and the release of the suture thread 12. In the embodiment shown in FIGS. 1 to 11, the locking member 16 is detachable from the casing 13. As shown in FIG. 4, the locking member 16 goes into its deactivated state when it is detached from the casing 13. In particular, the locking member 16 fits over an assembly portion 1300 of the base 130 like a locking shoe. To this end, as shown in FIG. 4, the locking member 16 comprises a bottom wall 160, two lateral walls 161 and a rear wall 162. The bottom wall 160 may be perforated to save on material. A front opening 163 and an upper opening 164 give the locking member 16 a shoe shape.

The assembly portion 1300 extends from the rear face 138 to a front portion 1301 of the base 130. The front portion 1301 includes, on the front face 137, the first opening 140 of the housing 14.

In addition, the anchor holder 10 comprises means for fitting the locking member 16 on the base 130. In this example, the fitting means include at least one rib 1302 which is positioned on the assembly portion 1300. As shown in FIGS. 4 and 5, the rib 1302 may extend longitudinally perpendicular to the axis A-A. In this instance, the fitting means include two ribs 1302 parallel to one another and positioned on each flank of the base 130. As can be seen in FIGS. 4 and 5, the fitting means may comprise lugs 1303. Each lug 1303 protrudes from a rib 1302. In this instance, a lug is arranged at each end of the rib 1302, a lower end which is proximal to the lower face 132 of the casing and an upper end which is proximal to the receptacle 131.

Furthermore, the fitting means include at least one slot 165 complementary to the rib 1302 so as to allow the locking member 16 to be fitted on and removed from the base 130. To this end, each slot 165 is formed in a lateral wall 161 of the locking member 16. In particular, each slot 165 extends along a longitudinal axis perpendicular to the axis A-A and each slot 165 is positioned on the lateral wall 161 in such a way as to slide on a rib 1302. The lugs 1303 allow better interaction between a slot 165 and a rib 1302.

Moreover, the anchor holder 10 may comprise indicators to ensure the method for assembling the anchor 11 on the attachment guide 30. For example, the locking member 16 comprises an arrow 166 marked with the numeral 1. This arrow 166 is oriented downward, pointing to the lower face 132 of the casing 13. The arrow 166 is an indicator, indicating to the practitioner that they must first pull the locking member 16 downward so as to unlock the anchor 11 and the suture thread 12. The arrow 166 thus indicates how to bring the locking member 16 from its activated state into its deactivated state. The assembly portion 1300 of the base 130 also bears an indicator for use of the anchor holder 10. Here again an arrow 1304 indicates to the practitioner the direction in which the anchor holder 10 must be moved along the attachment guide 30 so as to unwind the suture thread 12. In this example, the arrow 1304 is marked with the numeral 2. This is because it corresponds to a step which follows the removal of the locking member 16 and which is to be performed by the surgeon to complete the release of the suture thread 12 from the reel 15.

As shown in FIGS. 2, 7 and 9, the anchor holder 10 comprises a reel 15 which is configured to stow and release the suture thread 12. To this end, the reel 15 is in communication with the housing 14 so as to allow the passage of the suture thread 12. To this end, a passage 142 may be formed in the upper face 133 of the base 130. Thus, the receptacle 131 in which the reel 15 is stowed is in communication with the housing 14 in which the anchor 11 is stowed. The passage 142 is visible in FIG. 2 and in the cross section C-C of FIG. 10 which is shown in FIG. 11.

In this example, the reel 15 is mounted rotatably about an axis. To this end, the reel 15 is mounted on the rotation shaft of the reception means 136 of the receptacle 131.

The reel 15 includes at least one toothed wheel 150, 151, 152. As can be seen in FIG. 2 the reel 15 includes three toothed wheels 150, 151, 152 which are parallel to one another. In particular, the reel 15 comprises two lateral toothed wheels 150, 151 and a central toothed wheel 152 which is positioned at an equal distance from each of the lateral toothed wheels 150, 151. A first lateral toothed wheel 150 comprises an opening 153 at its center. This opening 153 is configured to receive the rotation shaft of the receptacle 131. In this regard, the opening 153 acts as a bearing for guiding the rotation of the reel 15 around said rotation shaft. The second lateral toothed wheel 151 also has an opening, but as can be seen in FIG. 2, this opening has a diameter greater than that of the opening 153.

In one embodiment, the reel 15 comprises at least one circular groove 154 around which the suture thread 12 is wound. The suture thread 12 is not shown in the circular groove 154 in FIGS. 1 to 8 so as to simplify the depiction of the invention. In the example of FIG. 2, the reel 15 comprises two circular grooves 154. Each circular groove 154 is delimited on one side by a lateral toothed wheel 150, 151 and on the other side by the central toothed wheel 152.

Moreover, the reel 15 may comprise means for removal from the receptacle 131, for example a withdrawal loop allowing an operator to pull on the reel 15 in a direction parallel to the axis of rotation with a view to removing the reel 15 from the receptacle 131. The withdrawal loop is not shown in the drawings, it may be threaded through two bores positioned on the lateral toothed wheel 151 which is visible when the reel 15 is inserted in the receptacle 131. In this example, the reel 15 comprises at least one slot 156 so as to block the suture thread 12. In this instance, the slot 156 extends radially on a toothed wheel 151, 152. In this instance, the second lateral toothed wheel 151 and the central toothed wheel 152 each include a slot 156. The two slots 156 of the reel 15 are coaxial. When the suture thread 12 is fully unwound, all that is required is to pull on the suture thread 12 to free it from the slot 156.

As can be seen in FIGS. 1 to 4, the locking member 16 includes a stop 167. This stop 167 is positioned on the rear wall 162 of the locking member 16. The stop 167 is configured to interact with at least one toothed wheel 150, 151, 152 so as to block the rotation of the reel 15. According to one embodiment, the stop 167 interacts with the teeth 155 of each toothed wheel 150, 151, 152 so as to block the rotation of the reel 15. To this end, the stop 167 has a shape complementary to the shape of the teeth 155.

Furthermore, the receptacle 131 includes a passage arranged on the rear face 138 of the casing 13 so as to allow to the stop 167 be inserted between two teeth 155 of at least one toothed wheel 150, 151, 152 so as to block the rotation of the reel 15. In the example of FIGS. 1 and 4, the receptacle 131 comprises a slot 139 which is formed in the peripheral wall 135. The slot 139 allows the stop 167 to be inserted between the teeth 155 of at least one toothed wheel 150, 151, 152. The rotation of the reel 15 is thus blocked as can be seen in particular in FIG. 3. Naturally, when the locking member 16 goes into its deactivated state, the stop 167 is disengaged from the reel 15 and allows it to rotate.

FIGS. 12 to 16 illustrate another embodiment of the anchor holder 10 of the invention in which the anchor 11 is an anchor in tissue. In the jargon of those skilled in the art this type of anchor may be called a "soft anchor". As shown in FIG. 12, the anchor 11 in tissue includes two sheaths 113 which are bent back on themselves. More specifically, the sheaths 113 are bent back on themselves and are linked to one another at the distal end 110 of the anchor 11. At the distal end 110, the fold in the sheaths 113 where they are bent back forms a structure which may be gripped by a forked pin. The fold corresponds to the assembly head 114 of the anchor 11. The distal end 110 is configured to be inserted in a pre-bore drilled in bone tissue. At the proximal end 111 of the anchor 11, the sheaths 113 are open so that a suture thread 12 passes through each sheath 113.

An anchor 11 in tissue is inserted forcibly into the bone with the aid of an impactor; once it has passed the cortical part of the bone, which is fairly hard, the anchor 11 in tissue penetrates the spongy part of the bone, and under the effect of a pulling force for removing the impactor, the tissue forms a ball with a diameter greater than the bore, which prevents the anchor 11 in tissue from coming out.

In this embodiment, the casing 13 also includes a receptacle 131 which is positioned above a base 130. The receptacle 131 is configured to accommodate a reel 15 and a passage 142 is formed between the receptacle 131 and the base 130 so as to allow the suture thread 12 to be stowed on the reel 15 while being connected to the anchor 11 which is stowed in the housing 14.

Figures 15, 16:
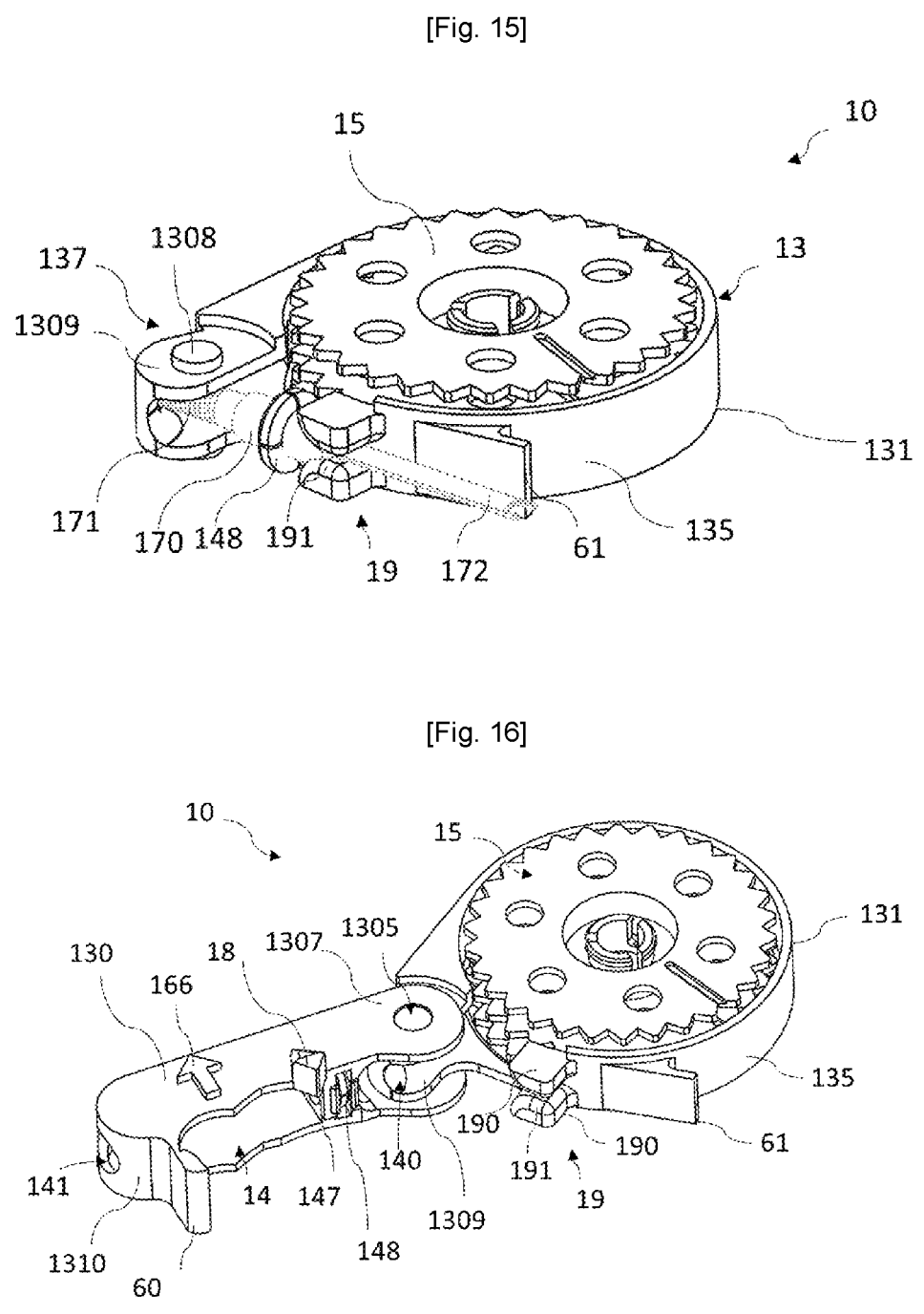

As shown in FIGS. 12, 14 and 15, the anchor holder 10 may include an interface 17 on which the anchor 11 in tissue is mounted. The interface 17 is configured to ensure precise assembly of the assembly end 300 of the attachment guide 30 with the anchor 11 in tissue. To this end, the interface 17 holds the anchor 11 in tissue in a predetermined position with a view to assembly with the attachment guide 30. For this purpose, the housing 14 comprises an annular passage 147 in which the interface 17 is positioned.

In this example, the interface 17 comprises a central body 170 extended, on a first side, by a connector 171, and on a second side, by an impacting support 172 which bears the anchor 11 in tissue and is configured to impact the anchor 11 in tissue in the bone.

The connector 171 is configured to be assembled with the assembly end 300 of the attachment guide 30. In this instance, the connector 171 is threaded, and in this configuration, the assembly end 300 may be formed by a socket the dimensions and the thread of which are complementary to the connector 171. However, the connector 171 may be produced by means of another mechanical connector of male or female type.

The connector 171 has a cross section smaller than the cross section of the central body 170. Thus, as can be seen in FIG. 12, the junction between the connector 171 and the central body forms a flange. Thus, within the housing 14, the connector 171 has a section which is smaller than the opening of the annular passage 147 while the flange is placed in abutment with the annular passage 147. The interaction between the interface 17 and the annular passage 147 helps hold the anchor 11 in tissue in a predetermined position.

The impacting support 172 for the anchor 11 in tissue in this case takes the form of a pronged pin onto which the assembly head of the anchor 11 in tissue is slipped as the two sheaths 113 are folded over on the pronged pin. The end of the pronged pin is placed against the bend in the sheaths 113. The impacting support 172 also has a cross section smaller than that of the central body 170. As shown in FIG. 12, the central body 170 comprises a bevel at the junction with the impacting support 172.

In the embodiment of FIGS. 12 to 16, the anchor holder 10 comprises two locking members 18, 19 which are arranged at the junction between the base 130 and the receptacle 131. In this instance, the locking members 18, 19 are movable between an activated state and a deactivated state. In their activated state shown in FIG. 13, the locking members 18, 19 block, on the one hand, the rotation of the reel 15, and on the other hand, the release of the anchor 11 in tissue.

In particular in this example, a first locking member 18 is rigidly secured to the base 130 and blocks the rotation of the reel 15 in the activated state. In this instance, the first locking member 18 consists of a tooth which interacts with the teeth of at least one of the toothed wheels 150, 151, 152 of the reel 15. The tooth acts as a stop for the reel 15; it is visible in FIGS. 12 to 14 and 16. In FIGS. 14 and 16, the tooth is not engaged with a toothed wheel 150, 151, 152 since the locking members 18, 19 are in the deactivated state.

In the embodiment shown in FIGS. 12 and 14 to 16, the second locking member 19 is rigidly secured to the peripheral wall 135 of the receptacle 131. This is particularly visible in FIGS. 15 and 16. In particular, the second locking member 19 is arranged at the junction between the base 130 and the receptacle 131 at the housing 14.

In this instance, the second locking member 19 consists of two cheeks 190 that are parallel to one another. The cheeks 190 protrude in the cavity of the housing 14, as can be seen in FIGS. 14 and 15. In this example, each cheek 190 has a domed internal surface 191 (see FIG. 16).

As can be seen in FIG. 15, the spacing between the cheeks 190 is configured to allow the passage of the impacting support 172 of the anchor 11 in tissue while preventing the passage of the central body 170. In particular, the domed internal surface 191 of each cheek 190 interacts with the bevel located at the junction between the central body 170 and the impacting support 172, in order to keep the interface 17 in position within the housing 14.

As shown in FIGS. 14 and 16, the base 130 is mounted movably relative to the receptacle 131. In particular, the base 130 is mounted rotatably relative to the receptacle 131. To this end, the base 130 may be articulated to the receptacle by means of a pivot connection 1305. On the one hand, the pivot connection 1305 may comprise two coaxial bearings 1306 arranged on two ears 1307 that are parallel to one another. The two ears 1307 respectively form part of a lateral wall 134 of the base 130. The two ears 1307 are positioned proximal to the front face 137 of the casing 13. On the other hand, the pivot connection 1305 comprises an axis which may be formed by two coaxial studs 1308 which are connected to the receptacle 131 and are arranged in such a way as to engage in the bearings 1306 arranged on the base 131. In this example, the studs 1308 are arranged respectively on a cheek 1309 that is rigidly secured to the receptacle 131. The two cheeks 1309 are parallel to one another and located proximal to the front face 137 of the casing 13. Furthermore, the two cheeks 1309 are connected to one another by a wall which extends on the front face 137 of the casing 13 and in which the first opening 140 is formed.

The interaction between the cheeks 1309 and the ears 1307 for forming the articulation makes it possible to maintain a free space between the cheeks 1309 which corresponds to the cavity of the housing 14, which allows the passage of the interface 17 and the rod 301 of the attachment guide 30.

The base 130 is thus movable between an open position and a closed position. In the closed position, the base 130 is rigidly secured to the receptacle 131 and, conversely, in the open position the rear part of the base 130 is radially at a distance from the receptacle 131 (see FIG. 14). In this embodiment the closed position of the base 130 corresponds to the activated state of the locking members 18, 19. The open position of the base 130 for its part corresponds to the deactivated state of the locking members 18, 19.

FIGS. 13 and 15 show the anchor holder 10 when the base 130 is in the closed position and the locking members are in their activated state. For example, FIG. 13 depicts the tooth of the first locking member 18 which is engaged with the teeth of the reel 15, this blocking the rotation of the reel 15 and, thereby, the release of the suture thread 12.

In FIG. 15, the base 130 is not shown so that the second locking member 19 is visible in its activated state. In this instance, the cheeks 190 clamp, via their domed internal surface 191, the interface 17 at the bevel forming the junction between the central body 170 and the impacting support 172. At the same time, the connector 171 is positioned in the housing 14 coaxial with the first opening 140. In this position, the cheeks 190 block the translational movement of the interface 17 and hence the removal of the anchor 11 in tissue from the housing 14 via the second opening 141.

FIGS. 14 and 16 show the base 130 in the open position. In the example of FIG. 14, when the base is in the open position, the interface 17 is released from the second locking member 19, which is in the deactivated state. The interface 17 may then be moved in translation by the attachment guide 30 (not shown) with a view to bringing the anchor 11 in tissue out of the housing 14 via the second opening 141. An arrow in dotted lines is visible in FIG. 14, and this arrow symbolizes the radial opening of the base 130 by rotation about the pivot connection 1305.

In FIG. 16, the base 130 is fully open, and it is thus possible to see the structure of the housing 14, and in particular of the annular passage 147, as well as of the locking members 18, 19, or of the first opening 140 positioned between the two cheeks 1309 which form the pivot connection 1305.

Consequently, in this configuration, the housing 14 is rotatable relative to the reel 15 because the base 130 is able to move relative to the receptacle 131.

In the embodiment shown in FIGS. 12 to 16, the anchor holder 10 may comprise a closure system. The closure system makes it possible to control the opening and the closing of the base 130 relative to the receptacle 131. The purpose of the closure system is to prevent any accidental opening of the base 130. In this example, the closure system includes a first element 60 mounted on the base 130, which is configured to be clipped onto a second element 61 arranged on the receptacle 131. In particular, the first element 60 is arranged at the top of a bulge 1310 positioned on the rear face 138 of the base 130 (see FIG. 13), the second opening 141 being formed at the lateral apex of the bulge 1310. As regards the second element 61 of the closure system, this is rigidly secured to the peripheral wall 135 of the receptacle 131. The position of the second element 61 on the peripheral wall 135 is defined in such a way as to interact with the first element 60 when the base 130 is in the closed position. Note that the bulge 1310 gives the practitioner something to grip onto so as to facilitate opening of the base 130.

According to this embodiment, the base 130 bears an arrow 166 oriented downward, indicating how to open the base 130 so as to unblock the anchor 11 in tissue and the suture thread 12.

According to this embodiment, the attachment kit 20 includes holding means which are configured to keep the suture thread 12 close to the rod 301 of the attachment guide 30 during the insertion of the anchor 11 in tissue in the bone tissue of the patient. In this instance, the holding means include the annular passage 147 in which the suture thread 12 passes. Moreover, the holding means include an O-ring 148 which is arranged in a slot 149 formed in the walls of the annular passage 147, this being shown in particular in the exploded view in FIG. 12. The O-ring 148 has a diameter of opening that is smaller than the diameter of the annular passage 147. Its elastic nature makes it possible to hold the suture thread 12 against the rod 301 of the attachment guide 30. To be specific, the annular passage 147 divides the housing into two compartments, a first compartment located on the side of the first opening 140 and a second compartment located on the side of the second opening 141. The suture thread 12 runs, via the passage 142, from the reel 15 in the first compartment of the housing 14, and is then connected to the anchor 11 in the second compartment, passing through the annular passage 147 and the O-ring. Note that the second locking member 19 extends in the second compartment of the housing 14.

The O-ring 148 makes it possible to keep the four strands of the two suture threads 12 close to the rod of the attachment guide 30 as the practitioner brings the end 300 of the attachment guide 30 up to the pre-bore.

As shown in FIGS. 1 to 7 and 9, the invention also relates to an attachment guide 30 which is complementary to the anchor holder 10 according to the invention.

FIG. 9 shows the attachment guide 30 on its own. During a surgical operation, the attachment guide 30 makes it possible in particular to screw the anchor 11 into the bone tissue 50. To this end, the attachment guide comprises an assembly end 300 which is configured to be assembled to the head of the anchor 11. In this example, the assembly end 300 is formed by two prongs of defined cross section. In particular, the cross section of each prong makes it possible to fit the assembly end 300 in the head of the anchor 11. By way of example, each prong may have a cross section made up of three sides which makes it possible to fit it in a head of an anchor 11 of hexagonal shape.

As shown in FIG. 9, the assembly end 300 constitutes the tip of a rod 301 of the attachment guide 30. Moreover, the attachment guide 30 comprises a sleeve 302 which allows practitioners to grasp and manipulate the attachment guide 30. As can be seen in particular in FIG. 9, the dimensions of the cross section of the sleeve 302 may be greater than the dimensions of the cross section of the rod 301.

In this example, the rod 301 extends longitudinally from the sleeve 302 to the assembly end 300 of the rod 301. As shown in FIG. 9, the attachment guide 30 comprises a slot 305, 306 which extends longitudinally at least between the assembly end 300 of the rod 301 and the sleeve 302. In the example of FIG. 9, a first slot 305 is formed on the rod 301 between the two ends of the rod 301 and extends along the longitudinal axis B-B. Moreover, the first slot 305 may be extended by a second slot 306 which is itself formed on the sleeve 302. The second slot 306 is coaxial with the first slot 305.

According to this configuration, the casing 13 of the anchor holder 10 is configured to slide on the rod 301 from the assembly end 300 to the sleeve 302. This is shown in FIGS. 5 and 6: the poka-yoke 145 of the housing 14 is configured to slide in the slot 305. For this purpose, the poka-yoke 145 has a shape complementary to the slot 305, for example a ridge of which the dimensions of the cross section are smaller than the dimensions of the cross section of the slot 305 so as to fit into and slide in the slot 305. Furthermore, the slot 305 is configured to receive the suture thread 12 which is released by the reel 15 when the casing 13 moves on the rod 301. This is visible in FIG. 7 in which the anchor 11 is inserted in the bone tissue as the reel 15 is placed in abutment on the sleeve 302, the suture thread 12 then extending from the anchor 11 to the reel 15, passing through the slot 305.

The present invention also relates to an attachment kit for attaching at least one suture thread to a biological tissue. This attachment kit comprises an anchor holder 10 and an attachment guide 30 both according to the invention. The anchor holder and the attachment guide 30 are configured to interact during a surgical operation to reconstruct ligaments or tendons. For example, the anchor holder 10 is movable in translation on the rod 301 of the attachment guide 30 when the housing 14 slides on the rod 301. Moreover, the slot 305 of the rod 301 is configured to receive the suture thread 12 when the anchor holder 10 is moved in the direction of the sleeve 302 on the rod 301 of the attachment guide 30.

The invention also relates to an assembly method 40 for assembling an attachment guide and an anchor equipped with at least one suture thread configured to be inserted in a biological tissue. According to the invention, the anchor and the suture thread are stowed in an anchor holder which may be according to the invention just like the attachment guide and the anchor.

Figure 17:
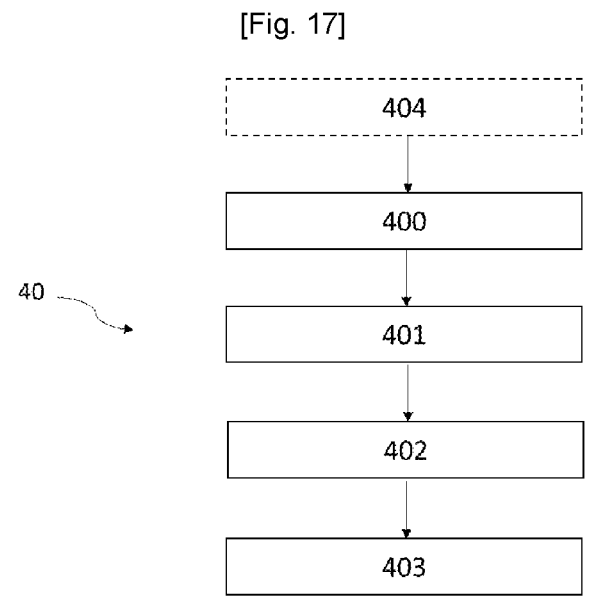

As shown in FIGS. 1 and 17, the assembly method 40 comprises a step of insertion 400 of the assembly end 300 of the rod of the attachment guide in the housing 14 of the attachment device 10. First, the anchor holder is removed from sterile packaging, while the attachment guide is itself sterilized. In this instance, the assembly end 300 is inserted via the first opening 140 of the housing 14. During this step 300, the poka-yoke 145 makes it possible to correctly position the assembly end 300 of the rod of the attachment guide so as to fit in the head of the anchor 11. In this example, the two prongs of the assembly end 300 must be positioned on either side of the poka-yoke 145 for the free end 300 to be able to enter the housing 14.

The assembly method 40 includes a step of assembly 401 of the assembly end 300 of the rod with the anchor 11. In practice, the assembly end 300, after insertion in the housing 14, is pushed to the bottom of the housing 14. In this example, the bottom of the housing 14 corresponds to the second opening 141 which at this stage of the assembly method 40 is obstructed by the locking member 16. The assembly end 300 is assembled by fitting onto the head of the anchor 11 which has an internal cross section complementary to the assembly end 300. According to the embodiment shown in FIGS. 12 to 16, the assembly end 300 may also be assembled to the anchor 11 in tissue by screwing via an interface 17.

As shown in FIGS. 4 and 17, the assembly method 40 comprises a step of deactivation 402 of the locking member 16, 18, 19 so as to release the anchor 11 and the suture thread 12. According to the example of FIG. 4, the locking member 16 goes from its activated state in which it is mounted on the base 130 of the casing 13 to its deactivated state in which the locking member 16 is detached from the base 130.

This step makes it possible, on the one hand, to open the second opening 141 of the housing 14 and to allow the anchor holder 10 to move, and on the other hand, to release the suture thread 12 stowed on the reel 15. In this example, the deactivated state of the locking member 16 makes it possible to release the rotation of the reel 15 which is mounted rotatably on the receptacle 131 of the casing 13.

In the embodiment of FIG. 14, the base 130 goes from its closed position to its open position to deactivate the locking members 18, 19 with a view to extracting the anchor 11 in tissue and releasing the rotation of the reel 15.

Furthermore, the assembly method 40 also comprises a step of movement 403 of the anchor holder 10 on the rod 301 in the direction of the sleeve 302 of the attachment guide 30. To this end, the anchor holder 10 slides with a longitudinal movement on the rod 301. The movement is produced by translation of the casing 13 on the rod 301 which is inserted in the cavity of the housing 14. The poka-yoke 145 may thus act as a slider to slide the casing 13 on the slot 305. In particular, during the movement of the anchor holder 10 the reel 15 releases the suture thread 12 when the anchor 11 is positioned at the assembly end 300 of the attachment guide. According to this embodiment, the suture thread 12 unwinds by virtue of the rotation of the reel 15 about its axis and the suture thread 12 then engages in the slot 305 of the rod 301. This is made possible by the passage 142 which communicates between the reel 15 and the cavity of the housing 14. As shown in FIG. 6, the anchor holder 10 is moved until it comes into abutment with the sleeve 302.

First of all, the assembly method 40 may include a step of sterilization 404 of the attachment guide 30. This step of sterilization 404 may be carried out using a chemical agent such as ethylene oxide or using a physical method such as irradiation with gamma rays.

The attachment kit is then ready for insertion of the anchor 11 borne by the attachment guide 30 in a pre-bore which is drilled beforehand with the aid of a suitable device such as a punch and/or a tap. To this end, the anchor 11 and more particularly its distal end 110 is positioned coaxially with the pre-bore. In the embodiment of FIGS. 1 to 8, the insertion is performed at least in part by screwing the threaded part of the anchor 11 into the pre-bore. By contrast, in the embodiment of FIGS. 12 to 16, the insertion is performed by an impact which is generated by an attachment guide 30 of impactor type. An impactor is an attachment guide 30 which includes an inner shaft that is movable in translation, and this shaft is connected, on the one hand, to the assembly end 300 of the attachment guide 30, and on the other hand, to a striking head which is at the end of the sleeve 302. The surgeon hits the striking head, generally with a mallet, to impact the bone tissue and cause the anchor 11 in tissue to penetrate under the cortical portion of the bone.

The impacting support 172 which bears the anchor 11 in tissue is thrust into the pre-bore, and on its removal, the tissue forms a ball against the cortical part of the bone, preventing the anchor 11 in tissue from coming out.

As can be seen in FIG. 7, once the anchor 11 has been screwed in the pre-bore, the rod 301 of the attachment guide 30 is disengaged from the head of the anchor 11. The anchor holder 10 is then removed from the rod 301 of the attachment guide 30, this being visible in FIG. 8. The practitioner may then unwind the suture thread 12 so as to finish off the repair operation.

The practitioner may then remove the reel 15 from the casing 13 by pulling on the disengagement means. The soft tissue (tendon or ligament) is connected with the aid of the suture thread 12 which may be provided with a needle for this purpose. Lastly, the soft tissue is brought closer to the bone tissue. When it is provided with a needle, the suture thread 12 cannot be removed from the reel 15 without the reel being taken out of the receptacle 131. To be specific, the needles do not pass through the passage 142 between the reel 15 and the housing. The surgeon may thus remove the reel 15 from receptacle 131 by pulling on the reel 15.

The invention claimed is:

1. An anchor holder for at least one suture thread in a biological tissue, the anchor holder comprising:
- an anchor equipped with an assembly head, the anchor being connected to a suture thread,
- a casing including a housing in which the anchor is stowed in a predetermined position, the housing comprising a first opening, the assembly head of the anchor being positioned coaxial with the first opening for allowing an insertion of an assembly end of an attachment guide into the housing, the assembly end of the attachment guide being complementary to the assembly head of the anchor,
- a reel which is configured to stow and release the suture thread, the reel being in communication with the housing so as to allow the passage of the suture thread, and
- one locking member which has an activated state and a deactivated state, in the activated state the one locking member simultaneously interacts with the housing for preventing the anchor from coming out of the casing from a second opening in the casing coaxial and opposite the first opening and engaging with the reel to prevent rotation of the reel and for preventing the suture thread from being released, while the deactivated state allows the anchor to come out of the second opening of the casing and the release of the suture thread.

2. The anchor holder as claimed in claim 1, wherein the reel is mounted rotatably about an axis and includes at least one toothed wheel.

3. The anchor holder as claimed in claim 2, wherein the locking member includes a stop which interacts with the toothed wheel so as to block the rotation of the reel.

4. The anchor holder as claimed in claim 1, wherein the reel comprises at least one circular groove around which the suture thread is wound.

5. The anchor holder as claimed in claim 1, wherein the anchor being stowed in a position proximal the second opening.

6. The anchor holder as claimed in claim 5, wherein the locking member obstructs the second opening.

7. The anchor holder as claimed in claim 1, wherein the locking member is detachable from the casing, the locking member going into its deactivated state when it is detached from the casing.

8. The anchor holder as claimed in claim 1, wherein the housing is mounted rotatably relative to the casing, the housing is movable between an open position and a closed position, wherein in the open position the housing is radially at a distance from the reel, and on the other hand, the closed position in which the housing is connected to the reel, and when the housing is in the closed position, the locking members are in their activated state and when the housing is in the open position, the locking members are in their deactivated state.

9. The anchor holder as claimed in claim 1, which includes a poka-yoke arranged in the housing at least in the first opening so as to insert the assembly end of the attachment guide with a predetermined orientation to allow assembly with the head of the anchor.

10. The anchor holder as claimed in claim 9, wherein the poka-yoke is formed of a ridge which extends longitudinally along the axis of the housing.

11. An attachment kit for attaching at least one suture thread to a biological tissue, the attachment kit comprising an anchor holder as claimed in claim 1 and the attachment guide which is sterilizable and reusable, wherein the attachment guide includes a sleeve extended by a rod ending in the assembly end that is configured to be assembled with the assembly head of the anchor which is stowed in the housing of the anchor holder.

12. The attachment kit as claimed in claim 11, wherein the anchor holder is translatably movable along on the rod of the attachment guide when the housing slides on the rod.

13. The attachment kit as claimed in claim 11, which includes a suture thread holder which is configured to hold the suture thread against the rod.

14. The attachment kit as claimed in claim 13, wherein the the suture thread holder includes a slot which extends longitudinally on the attachment guide, the slot being configured to receive the suture thread when the anchor holder is moved in the direction of the sleeve on the rod of the attachment guide.

15. A method for assembly of the attachment guide and of the anchor as claimed in claim 1, the assembly method comprising:

assembling the assembly end of the rod with the anchor, the assembly end of the rod of the sterilized attachment guide being inserted in the housing of the anchor holder until it fits with the assembly head of the anchor, deactivating the locking member in order to release the anchor and the suture thread, and moving the anchor holder on the rod in the direction of the sleeve, the anchor holder sliding via the housing on the rod in such a way as to place the suture thread under tension between the assembly end of the attachment guide and the anchor holder sliding on the rod.

16. An anchor holder for at least one suture thread in a biological tissue, the anchor holder comprising:

an anchor equipped with an assembly head, the anchor being connected to the at least one suture thread, a casing including a housing in which the anchor is stowed in a predetermined position, the housing comprising a first opening, the assembly head of the anchor being positioned coaxial with the first opening for allowing an insertion of an assembly end of an attachment guide into the housing, the assembly end of the attachment guide being complementary to the assembly head of the anchor, a reel which is configured to stow and release the suture thread, the reel being in communication with the housing so as to allow the passage of the suture thread, and at least one locking member which has an activated state and a deactivated state, the activated state preventing the anchor from coming out of the casing and the suture thread from being released, while, the deactivated state allowing the anchor to come out of the casing and the release of the suture thread, wherein the reel being mounted rotatably about an axis and includes at least one toothed wheel, the at least one locking member also includes a stop which interacts with the at least one toothed wheel, wherein the housing comprising a second opening opposite and coaxial with the first opening so that the housing passes through the casing, the anchor being stowed in a position proximal the housing on the side of to the second opening, wherein, in the activated state, the at least one locking member prevents the release of the suture thread by blocking the rotation of the reel by interacting with said at least one toothed wheel, wherein in the activated state the at least one locking member also preventing the anchor from coming out of the housing by obstructing the second opening.

* * * * *